United States Patent
Otsuka et al.

(10) Patent No.: US 10,513,820 B2
(45) Date of Patent: Dec. 24, 2019

(54) STAINPROOF FIBER STRUCTURE

(71) Applicant: TORAY INDUSTRIES, INC., Tokyo (JP)

(72) Inventors: Azuki Otsuka, Osaka (JP); Shinya Komori, Otsu (JP); Rumi Karasawa, Otsu (JP); Keiji Takeda, Otsu (JP)

(73) Assignee: Toray Industries, Inc. (JP)

( * ) Notice: Subject to any disclaimer, the term of this patent is extended or adjusted under 35 U.S.C. 154(b) by 230 days.

(21) Appl. No.: 15/736,049

(22) PCT Filed: Jul. 1, 2016

(86) PCT No.: PCT/JP2016/069600
§ 371 (c)(1),
(2) Date: Dec. 13, 2017

(87) PCT Pub. No.: WO2017/006849
PCT Pub. Date: Dec. 1, 2017

(65) Prior Publication Data
US 2018/0179699 A1    Jun. 28, 2018

(30) Foreign Application Priority Data

Jul. 6, 2015 (JP) .................. 2015-135033
Mar. 11, 2016 (JP) .................. 2016-048045

(51) Int. Cl.
*D06M 11/49* (2006.01)
*D06M 15/277* (2006.01)
(Continued)

(52) U.S. Cl.
CPC .......... *D06M 15/277* (2013.01); *D06M 11/49* (2013.01); *D06M 15/507* (2013.01);
(Continued)

(58) Field of Classification Search
CPC .................................................. D06M 11/49
See application file for complete search history.

(56) References Cited

U.S. PATENT DOCUMENTS

| 6,610,775 B1 | 8/2003 | Oharu et al. |
| 2014/0378018 A1 | 12/2014 | Kaneumi |

FOREIGN PATENT DOCUMENTS

| JP | 093771 A | 1/1997 |
| JP | 09324173 A | 12/1997 |

(Continued)

OTHER PUBLICATIONS

International Search Report and Written Opinion for International Application No. PCT/JP2016/069600, dated Sep. 20, 2016—7 Pages.

*Primary Examiner* — Andrew T Piziali
(74) *Attorney, Agent, or Firm* — RatnerPrestia

(57) ABSTRACT

A soil resistant fiber structure, including a fiber and a soil resistant resin fixed to at least a part of a surface of the fiber, wherein the resin has, in at least a part inside the resin, one or more regions dyed with osmium oxide as observed with a transmission electron microscope, at least one of the regions is circular, the regions have a maximum diameter of 100 nm or more and 500 nm or less, and the soil resistant fiber structure has a mass concentration ratio of oxygen atoms to fluorine atoms (O/F) of 3 or more as obtained by measuring the surface of the fiber with an energy dispersive X-ray analyzer. The present invention provides a fiber structure having high anti-adhesion property against aqueous soils and oily soils as well as soil release property by washing.

7 Claims, 1 Drawing Sheet

(51) Int. Cl.
*D06M 15/53* (2006.01)
*D06M 15/507* (2006.01)
(52) U.S. Cl.
CPC ........ *D06M 15/53* (2013.01); *D06M 2200/01* (2013.01); *D06M 2200/12* (2013.01)

(56) References Cited

FOREIGN PATENT DOCUMENTS

| | | | |
|---|---|---|---|
| JP | 1149825 | A | 2/1999 |
| JP | 2000212549 | A | 8/2000 |
| JP | 2005330354 | A | 12/2005 |
| JP | 2008062460 | A | 3/2008 |
| JP | 2008163475 | A | 7/2008 |
| JP | 2013036136 | A | 2/2013 |
| JP | 2013072165 | A | 4/2013 |
| JP | 2014163030 | A | 9/2014 |
| WO | 2013088902 | A1 | 6/2013 |

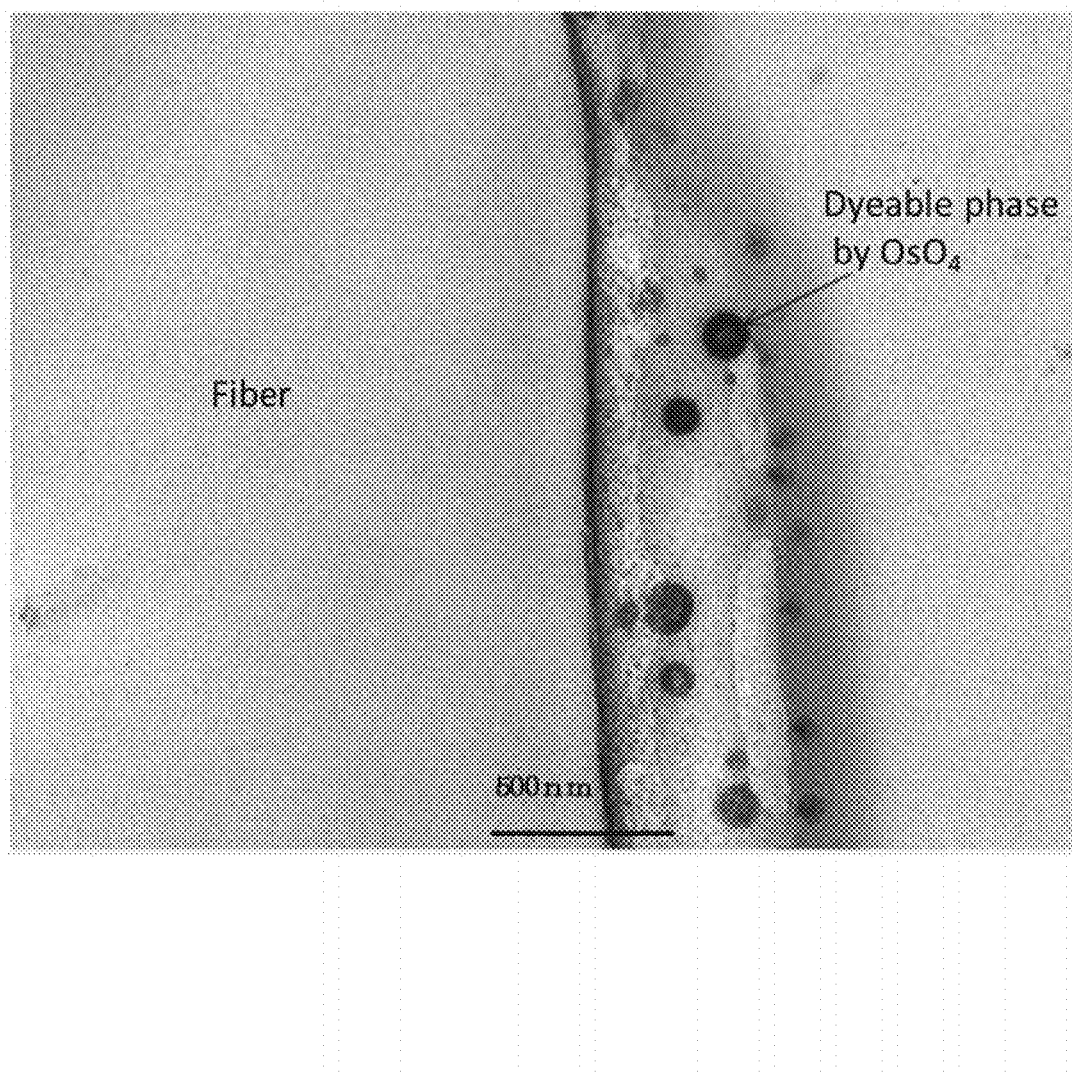

STAINPROOF FIBER STRUCTURE

CROSS REFERENCE TO RELATED APPLICATIONS

This is the U.S. National Phase application of PCT/JP2016/069600, filed Jul. 1, 2016, which claims priority to Japanese Patent Application No. 2015-135033, filed Jul. 6, 2015 and Japanese Patent Application No. 2016-048045, filed Mar. 11, 2016, the disclosures of each of these applications being incorporated herein by reference in their entirety for all purposes.

TECHNICAL FIELD OF THE INVENTION

The present invention relates to a fiber structure having high soil resistance.

BACKGROUND OF THE INVENTION

Conventionally, there has been high demand for an improvement in soil resistance of a fiber structure of a fabric such as a woven or knitted fabric, and various methods for improving the soil resistance have been proposed. In general, as a method for imparting soil resistance to a fiber structure, the following methods have been studied: a processing method of imparting a hydrophilic resin to a fiber structure for improving the affinity of the fiber structure to a washing liquid so as to facilitate release of a soil, and a processing technique of imparting a water- and oil-repellent resin to a fiber structure for suppressing adhesion of a soil to the fibers.

The method of imparting a hydrophilic resin to a fiber structure, however, has a problem that if an aqueous soil adheres to the fiber structure, the soil is likely to expand largely. In addition, the technique of imparting a water- and oil-repellent resin to a fiber structure has a problem that it is difficult to wash away a once adhered soil, and soil redeposition or the like is likely to occur, since the affinity of the fiber structure to a washing liquid is lowered due to the water repellency.

In view of these problems, it has been studied to impart a water- and oil-repellent resin containing a hydrophilic group to fibers in order to satisfy both the soil resistance and soil releasability.

PRIOR ART DOCUMENTS

Patent Documents

Patent Document 1 proposes a processing method of coating a fiber surface with a hydrophilic resin, and forming a layer of a water- and oil-repellent resin having a hydrophilic group on the hydrophilic resin.

Patent Document 2 proposes a processing method of forming a film containing a fluorine-based water repellent having a hydrophilic segment, to which a hydrophilic polymer is imparted by graft polymerization, on the surface of a fiber fabric.

Patent Document 3 proposes a processing method of forming a film made from a mixture of a polymer containing a triazine ring-containing polymerizable monomer and a fluorine-based water repellent having a hydrophilic component on the surface of single fibers.

In addition, Patent Document 4 proposes a processing method of imparting a fluorine-based water repellent to a fiber fabric using an unblocked aqueous dispersion type isocyanate cross-linking agent.

Patent Document 1: Japanese Patent Laid-open Publication No. 9-3771
Patent Document 2: Japanese Patent Laid-open Publication No. 2013-72165
Patent Document 3: Japanese Patent Laid-open Publication No. 2008-163475
Patent Document 4: Japanese Patent Laid-open Publication No. 2013-36136

SUMMARY OF THE INVENTION

The processing methods proposed in Patent Documents 1 and 2, however, have a problem that a once adhered aqueous soil is likely to expand, since the fiber surface is coated with a hydrophilic resin.

Further, in the processing method proposed in Patent Document 3, since the polymer containing a triazine ring-containing polymerizable monomer is used in a large amount, the component of the fluorine-based water repellent having a hydrophilic component is buried in the polymer containing a triazine ring-containing polymerizable monomer and thus cannot exhibit water repellency and oil repellency, and there is also a concern about the influence on the human body due to generation of formaldehyde.

In addition, since the fiber fabric in the processing method proposed in Patent Document 4 exhibits high water repellency, the method has a problem that the affinity of the fiber fabric to the washing liquid tends to be lowered during the washing, and the soil release property by washing tends to be deteriorated.

In view of the above-mentioned problems of conventional techniques, an object of the present invention is to provide a fiber structure having both high anti-adhesion property against aqueous soils and oily soils and soil release property by washing.

In order to solve the above-mentioned problems, the present invention has the following configuration. That is, the present invention provides:

A soil resistant fiber structure, including a fiber and a soil resistant resin fixed to at least a part of a surface of the fiber, wherein the resin has, in at least a part inside the resin, one or more regions dyed with osmium oxide as observed with a transmission electron microscope (hereinafter referred to as a TEM), at least one of the regions is circular, the regions have a maximum diameter of 100 nm or more and 500 nm or less, and the soil resistant fiber structure has a mass concentration ratio of oxygen atoms to fluorine atoms (O/F) of 3 or more as obtained by measuring the surface of the fiber with an energy dispersive X-ray analyzer.

Further, in the soil resistant fiber structure of the present invention, it is preferable that the resin have a plurality of the regions inside the resin, and the dyed regions be individually separated and scattered.

Further, in the soil resistant fiber structure of the present invention, it is preferable that the regions have a hydrophilic component and a hydrophobic component.

Further, in the soil resistant fiber structure of the present invention, it is preferable that the hydrophilic component be polyethylene glycol.

Further, in the soil resistant fiber structure of the present invention, it is preferable that the resin have a perfluorooctanoic acid (hereinafter sometimes referred to as PFOA) content less than a detection limit.

Further, in the soil resistant fiber structure of the present invention, it is preferable that the resin contain a compound represented by the following general formula (I) as a polymerization component:

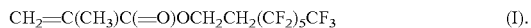

$$CH_2=C(CH_3)C(=O)OCH_2CH_2(CF_2)_5CF_3 \qquad (I).$$

In the soil resistant fiber structure of the present invention, it is preferable that the fiber structure have a soil release property in a soil release test of grade 3 or higher after 50 times of industrial wash.

According to the present invention, it is possible to stably provide a fiber structure having high soil resistance.

The soil resistant fiber structure of the present invention has a resin structure in which the ratio of the hydrophilic groups to the fluorine groups in the soil resistant resin on the fiber surface is controlled, the soil resistant resin has, in at least a part inside the resin, one or more hydrophilic regions, and at least one of the hydrophilic regions is circular and has a maximum diameter of 100 nm or more and 500 nm or less. Thus, it is possible to suppress adhesion of oily soils, that are difficult to wash away, to the fibers, and also to improve the affinity of the fiber structure to the washing liquid during the washing. Accordingly, it is possible to improve the soil release property by washing, and to shorten the washing time and reduce the detergent amount due to the high soil release property.

Further, adhesion of the soil resistant resin to the fiber surface by wet heat treatment reduces migration at the time of resin adhesion, and it is possible to impart high soil release property also to a fiber structure having a complicated structure.

BRIEF DESCRIPTION OF THE DRAWINGS

FIG. 1 is a TEM photograph of a cross-section of a single fiber used in the fiber structure obtained in Example 1, which is sliced in a direction perpendicular to the longitudinal direction of the fiber. The observation conditions of the TEM were an acceleration voltage of 100 kV and a magnification of 8000 times.

DETAILED DESCRIPTION OF CERTAIN EMBODIMENTS OF THE INVENTION

The soil resistant fiber structure of the present invention is a fiber structure including a fiber and a soil resistant resin fixed to at least a part of a surface of the fiber, wherein the resin has, in at least a part inside the resin, one or more regions dyed with osmium oxide as observed with a TEM, at least one of the regions is circular, and the regions have a maximum diameter of 100 nm or more and 500 nm or less.

Osmium oxide dyes a portion containing a hydrophilic component in the resin. In the fiber structure of the present invention, the region dyed with osmium oxide is formed from the hydrophilic component of the resin, and is present in at least a part inside the resin. Examples of the hydrophilic component include polyethylene glycol and polypropylene glycol. Above all, polyethylene glycol is preferable.

The soil resistant fiber structure of the present invention includes a soil resistant resin fixed to the fibers. The term "fix" means a state in which the resin is in contact with the fibers, the resin is adhered to the fibers, or the resin coats the fibers.

The dyed region needs to be circular. The term "circle" means a nonangular shape such as an ellipse, an oval, and a barrel shape. If the dyed region is not circular, the effect of the hydrophilic component cannot be sufficiently exhibited, so that there is a problem that the soil releasability during the washing is deteriorated.

It is preferable that the resin have a plurality of the dyed regions inside the resin from the viewpoint of securing a certain amount or more of a hydrophilic component to achieve excellent soil resistance. It is also preferable that a plurality of the dyed regions be scattered from the viewpoint of keeping the balance between hydrophilicity and hydrophobicity as well as improving soil resistance and washing durability of after the processing.

In order for the soil resistant fiber structure of the present invention to exhibit high soil resistance, it is preferable that the resin have a hydrophilic component and a hydrophobic component. It is possible to achieve both the soil resistance and soil releasability by optimizing the size of the region dyed with osmium oxide formed from the hydrophilic component. The hydrophilic component can improve the affinity between the fibers and the washing liquid, whereas the hydrophobic (oil-repellent) component can suppress penetration of soils into the fibers.

The region dyed with osmium oxide inside the resin as observed with a TEM needs to have a maximum diameter of 100 nm or more and 500 nm or less. If the maximum diameter of the region dyed with osmium oxide exceeds 500 nm, the water repellency and oil repellency are lowered, and the soil guard property of repelling soils is deteriorated. In addition, since the hydrophilic component region is excessively expanded, the adhesion between the resin and the fibers is lowered, resulting in deterioration of the washing durability. Meanwhile, if the maximum diameter of the region dyed with osmium oxide is less than 100 nm, the affinity of the fiber structure to the washing liquid during the washing is lowered, and the soil release property of releasing the soils is deteriorated.

The method of setting the maximum diameter within the above-mentioned range is not particularly limited. The soil resistant fiber structure of the present invention can be obtained by adjusting the content of the hydrophilic component.

In the following, a description will be given of dyeing with osmium oxide and a method for measuring the maximum diameter of the region dyed with osmium oxide inside the resin. First, the soil resistant fiber structure is immersed in 3% osmium oxide, dyed at normal temperature (20° C.) for 3 days, washed with water, and air dried. The sample is embedded in an epoxy resin.

Then, with use of a microtome, the fiber is sliced into a thickness of about 70 to 100 nm in a direction perpendicular to the longitudinal direction of the fiber. If it is difficult to cut the sample, the sample is cooled and then the fiber is sliced in the same manner. The cut sample piece is observed with a TEM (transmission electron microscope). The observation conditions of the TEM are an acceleration voltage of 100 kV and a magnification of 20000 times.

In the cross-sectional view obtained by slicing the fiber as described above, five regions dyed with osmium oxide in the resin fixed to the fiber surface are randomly selected, the maximum diameters of the regions are measured, and the average value thereof is calculated. When there are four or less regions dyed with osmium oxide, their maximum diameters are measured, and the average value thereof is calculated. Ten fibers randomly selected from the fiber structure are sliced, and the maximum diameters are calculated as described above for the total of ten fiber cross-sections. The average value thereof is regarded as the "maximum diameter of the region dyed with osmium oxide inside the resin as observed with a TEM".

In the present invention, it is preferable that the resin contain a hydrophobic component together with the above-mentioned hydrophilic component. Examples of the hydrophobic component include a fluororesin, a silicone resin, and a hydrocarbon resin. Among them, a fluororesin is preferably used because of high water- and oil-repellency.

The fluororesin preferably has a perfluorooctanoic acid (PFOA) content less than the detection limit. A fluorine-based water repellent having 6 carbon atoms (hereinafter referred to as a "C6 fluorine-based water repellent") is preferably used. Preferable examples of the C6 fluorine-based water repellent include $CH_2=C(CH_3)$ $C(=O)$ $OCH_2CH_2$ $(CF_2)_5CF_3$.

As the resin used in the present invention, a resin containing a copolymer of a hydrophilic component and a hydrophobic component is preferably used. As such a resin, a fluorine-based water repellent copolymerized with a hydrophilic component is preferably used, and one having a low water repellency not higher than grade 2 due to incorporation of a hydrophilic group is preferably used. A resin having a water repellency not higher than grade 2 can maintain the affinity between the fibers and the washing liquid to the minimum, allows the washing liquid to enter inside the fiber structure to come into contact with the soil without being repelled during the washing, and exhibits high soil resistance. The water repellency is a value obtained by evaluation according to the spray method defined in JIS L 1092 "Method for testing water repellency of textile products" (2009). Further, the water repellency can be adjusted to not higher than grade 2 by adjusting the content of the hydrophilic groups. Specific examples of the preferably used fluorine-based water repellent containing a hydrophilic component include "PARASIN" (registered trademark) KFS-100 (manufactured by KEIHIN CHEMICAL CO., LTD.), "PARARESIN" (registered trademark) NC-305 (manufactured by Ohara Paragium Chemical Co., Ltd.), and "PARASIN" (registered trademark) KFS-150 (manufactured by KEIHIN CHEMICAL CO., LTD.), which are commercially available.

The soil resistant fiber structure of the present invention has a mass concentration ratio of oxygen atoms to fluorine atoms (O/F) of 3 or more as obtained by measuring the surface of the fiber with an energy dispersive X-ray analyzer. If the mass concentration ratio of oxygen atoms to fluorine atoms (O/F) is less than 3, the amount of the hydrophobic component is large, so that the water repellency of the fibers is improved and the affinity of the fiber structure to the washing liquid is lowered. As a result, it is difficult for the washing liquid to come into contact with the soil, so that the soil release property by washing is deteriorated.

The range of the mass concentration ratio of oxygen atoms to fluorine atoms is preferably 3.1 to 5.0, more preferably 3.2 to 4.9, particularly preferably 3.3 to 4.0.

In order to obtain the mass concentration ratio of oxygen atoms to fluorine atoms, the mass concentrations are measured with an energy dispersive X-ray analyzer. The fiber structure of the present invention is subjected to measurement under the measurement conditions of low vacuum mode (30 Pa), an acceleration potential of 15.0 kV, a probe current of 70 A, and a measurement magnification of 100 times. The mass concentration ratio of oxygen atoms to fluorine atoms is calculated using the obtained mass concentrations of fluorine atoms and oxygen atoms. The following formula was used to calculate the mass concentration ratio of oxygen atoms to fluorine atoms (O/F). Each mass concentration is evaluated based on an average value of n=3 times.

O/F=mass concentration (% by mass) of oxygen atoms/mass concentration (% by mass) of fluorine atoms The soil resistant fiber structure of the present invention preferably has an oil repellency of grade 4 or higher as measured and graded by the method defined in AATCC (TM)-1966 in order to exhibit excellent soil resistance. The upper limit of the oil repellency is preferably grade 7, more preferably grade 6. These water repellency and oil repellency can be achieved by appropriately adjusting the ratio between the fluororesin and the hydrophilic groups.

The soil resistant fiber structure of the present invention preferably has a soil release property of grade 3 or higher in a "soil release test" according to the method C of JIS L 1919 (2006), "Soil release test", in which the component of lipophilic contaminant-3 defined therein is used, after 50 times of industrial wash.

Examples of the fiber material used in the soil resistant fiber structure of the present invention include fibers made from polyethylene terephthalate, polypropylene phthalate, and polybutylene terephthalate, aromatic polyester fibers obtained by copolymerizing these fibers with a third component, aliphatic polyester fibers typified by those containing L-lactic acid as a main component, polyamide fibers such as nylon 6 and nylon 66, acrylic fibers containing polyacrylonitrile as a main component, polyolefin fibers such as polyethylene and polypropylene, synthetic fibers such as polyvinyl chloride fibers, semisynthetic fibers such as acetate and rayon, and natural fibers such as cotton, silk, and wool. In the present invention, these fibers can be used singly or as a mixture of two or more thereof. It is preferable to use fibers containing polyester fibers or polyamide fibers as a main component, or a mixture of fibers containing polyester fibers or polyamide fibers as a main component and natural fibers such as cotton, silk, and wool.

Examples of the fibers used in the soil resistant fiber structure of the present invention include, in addition to the common flat yarns, filament yarns such as false twisted yarns, strong twisted yarns, taslan finished yarns, nanofibers, thick and thin yarns, and combined filament yarns, and various forms of fibers such as staple fibers, tows, and spun yarns can be used. Preferably, filament yarns are used.

Examples of the soil resistant fiber structure of the present invention include fabric-like materials such as knitted fabrics, woven fabrics, and nonwoven fabrics made from the above-mentioned fibers, and string-like materials. Preferably, a knitted fabric, a woven fabric, or a nonwoven fabric is used.

Further, a general finishing agent may be imparted to the fabric-like material or the string-like material. In addition, internally modified fibers may be used as the material of the soil resistant fiber structure. Examples of the usable finishing agent include pyridine compounds such as 2-chloro-6-trichloromethylpyridine, 2-chloro-4-trichloromethyl-6-methoxypyridine, 2-chloro-4-trichloromethyl-6-(2-furylmethoxy)pyridine, di(4-chlorophenyl)pyridylmethanol, 2,3,5-trichloro-4-(n-propylsulfonyl)pyridine, 2-pyridylthiol-1-oxide zinc, and di(2-pyridylthiol-1-oxide).

Further, as the material of the fabric-like material or the string-like material, fibers to which a resin other than the soil resistant resin is adhered may be used. In this case, a resin layer of the resin other than the soil resistant resin is formed on the fibers. Thus, two resin layers, that is, the formed resin layer and the subsequently formed soil resistant resin layer are present on the fibers. Examples of such resin other than the soil resistant resin include a silicone resin, a polyester resin, an isocyanate compound, an epoxy resin, a melamine resin, a guanamine resin, and a bismaleimide triazine resin.

Moreover, cross-linked and modified fibers may also be used. Examples of the preferable cross-linking agent used for cross-linking modification include compounds capable of reacting with hydroxyl groups in cellulose molecules making up a cellulosic fiber, in particular, hydroxyl groups in an amorphous region that cause wrinkles, deformation, or shrinkage during the washing to form a cross-linked structure between cellulose molecules and within cellulose molecules. Specific examples of such compound include formaldehyde, dimethylol ethylene urea, dimethylol triazone, dimethylol uron, dimethylol glyoxal monourein, dimethylol propylene urea, cellulose-reactive resins such as those obtained by methoxylating or ethoxylating part or all of methylol groups of these compounds, polycarboxylic acids, and isocyanates.

In the present invention, the resin can be fixed to the fiber structure by treating the fiber structure with a liquid containing a soil resistant resin. As a specific treatment method, the following treatment method can be employed: a pad dry cure method of immersing the fiber structure in a treatment liquid containing the soil resistant resin, and then squeezing the fiber structure in a spread state at a constant pressure, drying the fiber structure preferably at a temperature of 80 to 140° C., and then heat-treating the fiber structure preferably at a temperature of 160 to 200° C.; a pad cure method of drying the fiber structure at a temperature of 160 to 200° C. at once; a pad steam method of steaming the fiber structure at a temperature of 80 to 110° C.; and a bath method of raising the temperature of the treatment liquid containing a fluorine compound preferably to 30 to 130° C. in a state where the fiber structure is immersed in the treatment liquid.

In order for the soil resistant fiber structure of the present invention to exhibit high soil resistance, it is effective to achieve both the soil resistance and soil releasability by optimizing the ratio of the hydrophilic component containing oxygen to the hydrophobic component containing fluorine in the resin to be fixed to the fiber surface. The hydrophilic component can improve the affinity between the fibers and the washing liquid, whereas the hydrophobic component can suppress penetration of soils into the fibers.

As a resin to be fixed to the fiber surface, a resin containing a hydrophilic component and a hydrophobic component, specifically, as described above, for example, a resin obtained by copolymerizing polyethylene glycol with a fluorine compound is preferably used. The treatment liquid may also contain a silicone resin, a polyester resin, an isocyanate compound, an epoxy resin, or the like in combination.

In the present invention, it is a particularly preferable aspect to use a triazine ring-containing resin as a resin to be used in combination. Examples of the triazine ring-containing resin include a melamine resin, a guanamine resin, and a bismaleimide triazine resin. A melamine resin is particularly preferably used.

The "triazine ring-containing resin" means a resin containing a triazine ring-containing compound as a polymerization component. The triazine ring-containing compound is a compound containing a triazine ring and having at least two polymerizable functional groups. Examples of the triazine ring-containing compound include a triazine ring-containing compound represented by the following general formula:

[Chemical Formula 1]

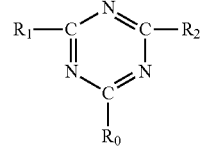

wherein $R_0$ to $R_2$ each represent H, OH, $C_6H_5$, $C_{n0}H_{2n0+1}$ (n0=1 to 2), $COOC_{n1}H_{2n1+1}$ (n1=1 to 20), $CONR_3R_4$, or $NR_3R_4$, wherein $R_3$ and $R_4$ each represent H, $OC_{n3}H_{2n3+1}$ (n3=1 to 20), $CH_2COOC_{n3}H_{2n3+1}$ (n3=1 to 20), $CH_2OH$, $CH_2CH_2OH$, $CONH_2$, or $CONHCH_2$—O—(X—O)$_{n4-R5}$ (X=$C_2H_4$, $C_3H_6$, or $C_4H_8$; n4=1 to 1500; and $R_5$=H, $CH_3$, or $C_3H_7$).

In addition to the triazine ring-containing compound represented by the general formula, ethylene urea copolymer compounds, dimethylol urea copolymer compounds, dimethylol thiourea copolymer compounds, and acid colloid compounds of the above-mentioned compounds can also be used.

The method for forming the triazine ring-containing resin is as follows. An aqueous solution containing the triazine ring-containing compound and a catalyst is applied to the fibers, and the fibers are subjected to heat treatment for polymerization.

Examples of the used catalyst include acids such as acetic acid, formic acid, acrylic acid, malic acid, tartaric acid, maleic acid, phthalic acid, sulfuric acid, persulfuric acid, hydrochloric acid, and phosphoric acid, and ammonium salts, sodium salts, potassium salts, and magnesium salts of these acids. One or more of these can be used. Among them, ammonium persulfate or potassium persulfate is preferably used as the catalyst. The amount of the catalyst is preferably 0.1 to 20% by mass based on the amount of the monomer.

The heat treatment for such polymerization is preferably carried out by dry heat treatment or steaming treatment at a temperature of 50 to 180° C. for 0.1 to 30 minutes. The steaming treatment is better at forming a uniform film on the single fiber surface and giving soft texture to the formed film. For such steaming treatment, saturated steam or superheated steam at 80 to 160° C. is preferably used. More preferably, saturated steam at 90 to 130° C. or superheated steam at 110 to 160° C. is used. In either case, the treatment is carried out for several seconds to several minutes. After such steaming treatment, washing with hot water at a temperature of 50 to 95° C. or washing with a nonionic surfactant or sodium carbonate is preferably carried out in order to remove unreacted monomers and catalyst and to ensure fastness to dyeing. The adhesion amount of the triazine ring-containing resin is preferably 0.5 to 5% by mass, more preferably 1 to 3% by mass based on the fiber mass.

In the case of forming a layer containing the above-mentioned fluororesin containing a hydrophilic component and a triazine ring-containing resin, the layer can be formed by carrying out the same treatment as described above using a mixed solution of a triazine ring-containing resin and a fluororesin. The mass ratio of the fluororesin to the triazine ring-containing resin in the mixture (fluororesin/triazine ring-containing resin) is preferably 1/0.001 to 1.

The soil resistant fiber structure of the present invention can be obtained by adhering the soil resistant resin to the fiber surface. In order to achieve both the high soil release property and washing durability, it is preferable to control the amount of the fixed resin. Specifically, the rate of the fixed soil resistant resin based on the fiber weight is preferably 0.6 to 1.0%, more preferably 0.7 to 0.9% in terms of solid content. When the rate of the fixed resin is within such a preferable range, the soil release property can be sufficiently exhibited, and there is no possibility that the fibers have a hard texture.

The soil resistant fiber structure of the present invention is suitably used in general clothing items, working uniforms, bedding products, medical garments, interior goods, industrial materials and the like, since the fiber structure exhibits the soil release property by washing and washing durability. Above all, the soil resistant fiber structure is suitably used in working uniforms which are likely to catch oily soils hardly releasable by washing and are required to have soil resistance.

In addition, due to the high soil release property, the soil resistant fiber structure of the present invention can shorten the washing time and reduce the detergent amount. The soil resistant fiber structure exhibits, in home wash in accordance with JIS L 0217 103, a result of the soil resistance test of grade 3 or higher when a washing machine having a MA value (physical force) in the washing process alone of 15 (NA-F50Z8 manufactured by National) is used and the washing time is shortened so that the MA value in the washing process would be 5 (washing time: 1 minute and 30 seconds). The soil resistant fiber structure exhibits, also in industrial wash, a result of the soil resistance test of grade 3 or higher when a washing machine having a MA value (physical force) of 51 (Ecoromato 10 manufactured by ASAHI SEISAKUSHO CO., LTD.) is used and the washing time is shortened so that the MA value would be 19 (washing time: 1 minute). As a result of this effect, the amount of greenhouse gas reduction per 57 times of washing of one piece of clothing (440 g) made of the soil resistant fiber structure is 0.47 kg $CO_2$-eq for industrial wash and 0.23 kg $CO_2$-eq for home wash compared to the case of an unprocessed product. In addition, even in the case of home wash with half the detergent amount of JIS L 0217 103, the soil resistant fiber structure exhibits a result of the soil resistance test of grade 3 or higher, and in the case of industrial wash with half the detergent amount, the soil resistant fiber structure exhibits a result of the soil resistance test of grade 3 or higher. As a result of this effect, the amount of greenhouse gas reduction per 57 times of washing of one piece of clothing (440 g) made of the soil resistant fiber structure is 0.44 kg $CO_2$–eq for industrial wash and 0.21 kg $CO_2$–eq for home wash compared to the case of an unprocessed product.

EXAMPLES

In the following, the soil resistant fiber structure of the present invention will be described with reference to the examples. Various measurements and evaluations in the examples were carried out in the following manner.

(Observation of Internal Structure of Resin by TEM)

A soil resistant fiber structure was immersed in 3% osmium oxide, dyed at normal temperature (20° C.) for 3 days, washed with water, and air dried. The sample was embedded in an epoxy resin. Then, with use of a microtome, the fiber was sliced into a thickness of about 70 to 100 nm in a direction perpendicular to the fiber length. The cut sample piece was observed with a TEM (transmission electron microscope) H-7100FA (manufactured by Hitachi, Ltd.). The observation conditions of the TEM were an acceleration voltage of 100 kV and a magnification of 8000 times.

In the cross-sectional view obtained by slicing the fiber as described above, five regions dyed with osmium oxide in the resin fixed to the fiber surface were randomly selected, the maximum diameters of the regions were measured, and the average value thereof was calculated. When there were four or less regions dyed with osmium oxide, their maximum diameters were measured, and the average value thereof was calculated. Ten fibers randomly selected from the fiber structure were sliced, and the maximum diameters were calculated as described above for the total of ten fiber cross-sections. The average value thereof was regarded as the "maximum diameter of the region dyed with osmium oxide as observed with a TEM". In the case where there was no circular region dyed with osmium oxide, the result was indicated as "-"

(Measurement of Mass Concentrations of Oxygen and Fluorine for Fluorine Compound)

A treated white fabric was cut into about 1 cm×1 cm, and the mass concentration was measured with an energy dispersive X-ray analyzer. Each sample was subjected to measurement under the measurement conditions of low vacuum mode (30 Pa), an acceleration potential of 15.0 kV, a probe current of 70 A, and a magnification of 100 times. The mass concentration ratio of oxygen atoms to fluorine atoms (O/F) was calculated by dividing the obtained mass concentration of oxygen atoms (% by mass) by the mass concentration of fluorine (% by mass). Each mass concentration was evaluated based on an average value of n=3 times.

(Water Repellency)

The water repellency was graded by evaluation according to the spray method defined in JIS L 1092 "Method for testing water repellency of textile products" (2009). The grade was determined based on an evaluation of n=once. The grade numbers in parentheses indicate that the back of the fabric is also wet. Grades of water repellency are grade 1 to grade 5. The larger the numerical value is, the higher the water repellency is. The determination is made based on the determination pictures attached to JIS L 1092 as the criteria.

(Oil Repellency)

The oil repellency was graded by measurement according to the method defined in AATCC TM-1966. Grades of oil repellency are grade 1 to grade 8. The larger the numerical value is, the higher the oil repellency is. The determination is made based on the determination pictures attached to AATCC TM-1966 as the criteria. The grade was determined based on an average value of evaluation of n=3 times.

(Soil Release Property)

The fiber structure obtained in each of the examples and comparative examples was washed 50 times under industrial wash conditions described later. Then, the fiber structure was evaluated for the soil release property according to the soil releasability test with dripping and wiping test defined in the method C of JIS L 1919, "Soil resistance test method of textile products" (2006), and the soil release property was graded. The grade of soil resistance is determined by naked eye using the JIS gray scale for contamination color. Grades of soil resistance are grade 1 to grade 5. The larger the numerical value is, the higher the soil resistance is.

(Industrial Wash Conditions in Soil Release Test)

Industrial wash (once) was carried out under the following conditions in the following order for the evaluation of washing durability and soil release property in the soil release test.

1. Wash (water temperature: 60° C., bath ratio: 1:10, time: 15 minutes)

Detergent: Phosphorus-free "Dash" (registered trademark) 2.0 g/L

After standing, the contaminated fabrics were sewed together into a size of about 40 cm×40 cm, and washed. If the contaminated fabrics were not enough, waste cloths were sewed together. The grade of SR property was determined by naked eye using the gray scale for contamination color of JIS L 0805. Grades of soil resistance are grade 1 to grade 5. The larger the numerical value is, the higher the soil resistance is. The equipment used in the above-mentioned test is shown in Table 1.

TABLE 1

| | Used substrates | Manufacturer | Remarks (used amount) |
|---|---|---|---|
| Contaminant | Olive oil | Wako Pure Chemical Industries, Ltd. | (61.5 g) |
| | Oleic acid | Sigma-Aldrich Japan | (37.0 g) |
| | Iron oxide (III) for ferrite | Wako Pure Chemical Industries, Ltd. | (1.0 g) |
| | Oil red | Sigma-Aldrich Japan | (0.1 g) |
| Equipment for Test | Square filter paper | ADVANTEC | 600 × 600 mm, Qualitative filter No. 2 |
| | Circular filter paper | Sansho Co., Ltd. | Diameter: 11 cm, Grade 389 Whatman paper filter No. 41 ϕ 110 1441-110 100 pieces |
| | Film for Overhead Projector | KOKUYO | Film for Overhead Projector, VF-1 |
| | Load | | 5 cm × 5 cm, 100 g | sodium metasilicate 2.0 g/L

"Clewat" (registered trademark) N 1.0 g/L

2. Spin-drying (time: 1 minute)
3. Rinsing 1 (water temperature: 50° C., bath ratio: 1:10, time: 3 minutes)
4. Spin-drying (time: 1 minute)
5. Rinsing 2 (water temperature: 35° C., bath ratio: 1:10, time: 3 minutes)
6. Spin-drying (time: 1 minute)
7. Rinsing 3 (normal water temperature, bath ratio: 1:10, time: 3 minutes)
8. Spin-drying (time: 1 minute)
9. Tumble drying (Soil Release Property)

As for the fiber structure after 50 times of industrial wash under the above-mentioned conditions, the soil release property according to the method C of JIS L 1919, "Soil resistance test method of textile products" (2006) was evaluated. A contaminant (oil red fraction: 0.1%) was produced using the component of lipophilic contaminant-3 defined in the method C of JIS L 1919, "Soil resistance test method of textile products" (2006), and the test was carried out according to the following procedure.

A PET film was placed on a square filter paper piece, and a fabric cut into 8 cm×8 cm was placed thereon. From a height of 10 cm, 0.1 mL of an oily soil was dropped, and the fabric was left to stand for 30 seconds.

A PET film cut into the same size as that of the contaminated fabric was placed on the fabric, and a weight of 100 g was applied thereto for 30 seconds. The weight and the film were removed, and then a circular filter paper piece was put on the fabric, and the soil was sucked up by the weight of the filter paper. Then, the position of the filter paper piece was shifted, and the soil was sucked up again with a clean portion of the filter paper. This operation was repeated until the filter paper piece would not absorb the soil any more. If the filter paper piece did not touch the contaminated part, both the ends of the filter paper piece were held and the soil was sucked by bringing the filter paper piece into contact with the soil so as not to apply weight as much as possible. Then, the fabric was left to stand for 24 hours under the conditions of a temperature of 20° C. and a humidity of 65%.

(Industrial Wash Conditions in Antibacterial Test)

Industrial wash (50 times) was carried out under the following conditions in the following order for the evaluation of washing durability in the antibacterial test.

1. Wash (water temperature: 80° C., bath ratio: 1:30, time: 120 minutes)

Detergent: JAFET standard formulation detergent 120 mL (for 90 L of water)

2. Spin-drying (time: 3 to 5 minutes)
4. Overflow rinsing (normal water temperature, bath ratio: 1:30, time: 15 minutes)
5. Spin-drying (time: 3 to 5 minutes)
6. Repeat steps 4 and 5 3 times (total of 4 times)
7. Repeat steps 1 to 6 5 times
8. Overflow rinsing in household washing machine for 5 minutes (normal water temperature, bath ratio: 1:30)
9. Spin-drying (time: 3 to 5 minutes)
10. Tumble drying (80° C. or lower)

(Antibacterial Test Method)

The unified test method was adopted as the test method, and an MRSA clinical isolate was used as the test bacterial bodies. In the test method, a bouillon suspension of the test bacteria was poured onto a sterilized sample fabric, the viable bacteria count after culturing at 37° C. for 18 hours in a closed container was counted, the number of bacteria relative to the number of grown bacteria was obtained, and the antibacterial property was evaluated according to the following criteria.

Under the condition of $\log(B/A) > 1.5$, $\log(B/C)$ was set as the difference in bacteria count increase/decrease, and a value of 2.2 or more was regarded as the acceptable level. In the examples, accepted products are designated as "good", and rejected products are designated as "failure".

In the formula, A represents the number of bacteria of an unprocessed product dispersed and recovered immediately after inoculation, B represents the number of bacteria of an unprocessed product dispersed and recovered after culturing for 18 hours, and C represents the number of bacteria of a processed product dispersed and recovered after culturing for 18 hours.

(Prevention of Bleeding Property)

A solid oily soil was applied in a thickness of 1 mm to a range of 5×5 cm on a film, and sterilized gauze (sterilized gauze type III "K-PINE" (registered trademark) No. 7164, manufactured by Kawamoto Corporation, 5.0 cm×5.0 cm, 1 piece) was placed on the film. On the sterilized gauze, a fabric sample of 8×8 cm was placed, and a filter paper piece (manufactured by SANSYO Co., LTD) and a weight of 0.4 kPa, 5.0×5.0 cm were further placed thereon in this order. The resultant laminate was left to stand at 37° C. for 24 hours, and the presence or absence of bleeding of the solid oily soil to the filter paper piece was visually determined.

In Table 4, a sample with no bleeding is designated as "good", and a sample with bleeding is designated as "failure".

<Components of Solid Oily Soil>
  White vaseline (manufactured by KENEI Pharmaceutical Co., Ltd.): 99.9% by mass
  Oil Red (manufactured by Wako Pure Chemical Industries, Ltd.): 0.1% by mass (Minimum MA Value for Achieving Soil Release Property of Grade 4)

In the soil release test, the shortest washing time at which the soil release property in home wash in accordance with JIS L 0217 103 (revised 1995, detergent amount: 1.0 g/L) was grade 4 or higher was measured, and the physical quantity in this case was represented as a MA (mechanical action) value. The MA value was obtained by washing a MA test fabric made of a plain weave cotton fabric of 25 cm×25 cm having 5 round holes of 35 mm in diameter at the center and four corners of the fabric, and counting the total number of yarns frayed at the edges of the 5 holes as the MA value.

(Amount of Greenhouse Gas Reduction by Shortening of Washing Time)

The washing time at which the soil release property in the soil release test was grade 4 or higher was measured. Assuming that the power consumption per hour of the washing machine is 470 Wh, and the power consumption during 28 minutes of washing (washing, rinsing, and spin-drying) is constant, the power consumption was provisionally calculated from the washing time at which the soil release property was grade 4 or higher. From the provisionally calculated power consumption, the volume of greenhouse gas emission was calculated according to the database of the LCA support software MiLCA (Tokyo Electric Power Company), and the difference from the volume in the case of an unprocessed product was taken as the amount of greenhouse gas reduction.

(Amount of Greenhouse Gas Reduction by Reduction of Detergent Amount)

The washing time at which the soil release property in the soil release test was grade 4 or higher was measured. The detergent amount that was reduced compared to the case of 2.0 g/L of Phosphorus-free "Dash" (registered trademark), 2.0 g/L of sodium metasilicate, and 1.0 g/L of "Clewat" (registered trademark) N was calculated. The volume of greenhouse gas emission was calculated according to the database of the LCA support software MiLCA using a synthetic laundry detergent (Phosphorus-free "Dash" (registered trademark)), sodium silicate (sodium metasilicate), and a chelating agent ("Clewat" (registered trademark) N), and the difference from the volume of greenhouse gas emission when a standard amount of the detergent is used was taken as the amount of greenhouse gas reduction.

Example 1

A twill fabric was woven using false twisted yarns made from polyethylene terephthalate having a total fineness of 84 dtex and composed of 72 filaments as a warp and a weft. The obtained twill fabric was scoured in a scouring machine at a temperature of 95° C. by a routine method, washed with hot water, and then dried at a temperature of 130° C. Then, the twill fabric was dyed with a liquor flow dyeing machine to fluorescent white at a temperature of 130° C., washed by a routine method, washed with hot water, dried, and heated at a temperature of 170° C. to produce a white fabric.

Then, 60 g/L of (A) PARASIN KFS-100 (a fluororesin manufactured by KEIHIN CHEMICAL CO., LTD., solid content: 10%) containing perfluorooctyl methacrylate and polyethylene glycol as polymerization components, 3.0 g/L of (L) "BECKAMINE" (registered trademark) M-3 (a triazine ring-containing compound manufactured by DIC Corporation, solid content: 80%), and 0.5 g/L of (M) Catalyst ACX (a catalyst manufactured by DIC Corporation, solid content: 35%) were dissolved to adjust a treatment liquid. The white fabric produced as described above was immersed in the treatment liquid, squeezed with a mangle to a squeezing rate of 90%, dried at a temperature of 130° C., and then heat-treated at a temperature of 170° C. The soil release property of the obtained soil resistant fiber structure after 50 times of industrial wash was grade 4 to 5 by gray scale for assessing staining. The fluorine compound adhered to the fibers repelled the soil, and a region of polyethylene glycol forming a plurality of circular dyed regions having a maximum diameter of 100 nm or more and 500 nm or less included in the fluorine compound maintained the affinity to the washing liquid during the washing without affecting the affinity of the fluorine compound to the fiber surface. Accordingly, the twill fabric had both the high soil release property and washing durability.

Example 2

A soil resistant fiber structure was obtained in the same manner as in Example 1, except that (B) "PARARESIN" (registered trademark) NC-305 (a fluororesin manufactured by Ohara Paragium Chemical Co., Ltd., solid content: 10%) containing a fluorine-based vinyl monomer having a fluoroalkyl group having 6 or less carbon atoms and a polyalkylene glycol-containing hydrophilic vinyl monomer as polymerization components was used as the fluororesin in place of PARASIN KFS-122 in Example 1. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 3 to 4 by gray scale for assessing staining. This is based on the same principle as in Example 1.

Example 3

A soil resistant fiber structure was obtained in the same manner as in Example 1, except that (C) PARASIN KFS-150 (a fluororesin manufactured by KEIHIN CHEMICAL CO., LTD., solid content: 10%) containing perfluorooctyl methacrylate and polyethylene glycol as polymerization components was used as the fluororesin in place of PARASIN KFS-122 in Example 1. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 3 by gray scale for assessing staining. Based on the same principle as in Example 1, the soil resistant fiber structure had both the high soil release property and washing durability.

Example 4

A twill fabric was woven using false twisted yarns made from polyethylene terephthalate having a total fineness of 84 dtex and composed of 72 filaments as a warp and a weft.

Then, as an antibacterial agent, 50 g of (O) 2-pyridylthiol-1-oxide zinc, 20 g of (P) a naphthalenesulfonic acid formalin condensate, and 30 g of (Q) sodium lignin sulfonate were slurried together with 300 g of water. Then, the slurry was subjected to a wet milling process with glass beads to give a colloidal composition having an average particle size of 1 µm. The test fabric was immersed in a liquid of pH 5 having a bath ratio of 1:10 and containing 1% owf of the colloidal antibacterial agent, 2% owf of a fluorescent whitish dispersive dye, and 0.5 g/L of a level dyeing agent, and dyed by a routine method under the conditions of 130° C. and 60 minutes. Then, the fabric was washed with water and dried at 170° C. for 2 minutes to give an antibacterial fabric.

Then, 60 g/L of (A) PARASIN KFS-100 (a fluororesin manufactured by KEIHIN CHEMICAL CO., LTD., solid content: 10%) containing perfluorooctyl methacrylate and polyethylene glycol as a fluororesin, 3.0 g/L of (L) "BECK-AMINE" (registered trademark) M-3 (a triazine ring-containing compound manufactured by DIC Corporation, solid content: 80%), and 0.5 g/L of (M) Catalyst ACX (a catalyst manufactured by DIC Corporation, solid content: 35%) were dissolved to adjust a treatment liquid. The white fabric produced as described above was immersed in the treatment liquid, squeezed with a mangle to a squeezing rate of 90%, dried at a temperature of 130° C., and then heat-treated at a temperature of 170° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. Based on the same principle as in Example 1, the soil resistant fiber structure had both the high soil release property and washing durability.

Example 5

A twill fabric was woven using false twisted yarns made from polyethylene terephthalate having a total fineness of 84 dtex and composed of 72 filaments as a warp and a weft. The obtained twill fabric was scoured in a scouring machine at a temperature of 95° C. by a routine method, washed with hot water, and then dried at a temperature of 130° C. Then, the twill fabric was dyed with a liquor flow dyeing machine to fluorescent white at a temperature of 130° C., washed by a routine method, washed with hot water, dried, and heated at a temperature of 170° C. to produce a white fabric.

Then, 50 g/L of (O) 2-pyridylthiol-1-oxide zinc as an antibacterial agent was diluted to adjust a treatment liquid. The white fabric produced as described above was immersed in the treatment liquid, squeezed with a mangle to a squeezing rate of 90%, dried at a temperature of 120° C., and then heat-treated at a temperature of 170° C.

Then, 60 g/L of (A) PARASIN KFS-100 (a fluororesin manufactured by KEIHIN CHEMICAL CO., LTD., solid content: 10%) containing perfluorooctyl methacrylate and polyethylene glycol as a fluorine compound, 3.0 g/L of (L) "BECKAMINE" (registered trademark) M-3 (a triazine ring-containing compound manufactured by DIC Corporation, solid content: 80%), and 0.5 g/L of (M) Catalyst ACX (a catalyst manufactured by DIC Corporation, solid content: 35%) were dissolved to adjust a treatment liquid. The fabric was immersed in the treatment liquid, squeezed with a mangle to a squeezing rate of 90%, dried at a temperature of 130° C., and then heat-treated at a temperature of 170° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. Based on the same principle as in Example 1, the soil resistant fiber structure had both the high soil release property and washing durability.

Example 6

A twill fabric was woven using 34's count two-fold yarns made from 80% of polyethylene terephthalate and 20% of cotton as a warp, and false twisted yarns made from polyethylene terephthalate having a total fineness of 84 dtex and composed of 72 filaments as a weft. A soil resistant fiber structure was obtained in the same manner as in Example 1, except that a white fabric obtained by dyeing the obtained twill fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 7

A twill fabric was woven using 34's count two-fold yarns made from 80% of polyethylene terephthalate and 20% of cotton as a warp, and false twisted yarns made from polyethylene terephthalate having a total fineness of 84 dtex and composed of 72 filaments as a weft. A soil resistant fiber structure was obtained in the same manner as in Example 4, except that a white fabric obtained by dyeing the obtained twill fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 8

A twill fabric was woven using 34's count two-fold yarns made from 80% of polyethylene terephthalate and 20% of cotton as a warp, and false twisted yarns made from polyethylene terephthalate having a total fineness of 84 dtex and composed of 72 filaments as a weft, whereby a soil resistant fiber structure was obtained. The same procedure as in Example 5 was repeated, except that a white fabric obtained by dyeing the obtained twill fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 9

A twill fabric was woven using 34's count two-fold yarns made from 80% of polyethylene terephthalate and 20% of cotton as a warp, and false twisted yarns made from polyethylene terephthalate having a total fineness of 84 dtex and composed of 72 filaments as a weft. A white fabric was produced by dyeing the obtained twill fabric in an ordinary dyeing process.

Then, 100 g/L of (R) an aqueous dimethylol dihydroxy ethylene urea resin solution (solid content: 20%) as a cross-linking agent, and 20 g/L of (S) magnesium chloride as a catalyst were diluted to adjust a treatment liquid. The white fabric produced as described above was immersed in the treatment liquid, squeezed with a mangle to a squeezing rate of 90%, dried at a temperature of 100° C., and then heat-treated at a temperature of 170° C.

Then, 60 g/L of (A) PARASIN KFS-100 (a fluororesin manufactured by KEIHIN CHEMICAL CO., LTD., solid content: 10%) containing, as polymerization components, perfluorooctyl methacrylate and polyethylene glycol as a fluororesin, 3.0 g/L of (L) "BECKAMINE" (registered trademark) M-3 (a triazine ring-containing compound manufactured by DIC Corporation, solid content: 80%), and 0.5 g/L of (M) Catalyst ACX (a catalyst manufactured by DIC Corporation, solid content: 35%) were dissolved to adjust a treatment liquid. The fabric was immersed in the treatment liquid, squeezed with a mangle to a squeezing rate of 90%, dried at a temperature of 130° C., and then heat-treated at a temperature of 170° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. Based on the same principle as in Example 1, the soil resistant fiber structure had both the high soil release property and washing durability.

Example 10

A plain weave fabric was woven using 34's count two-fold yarns made from 65% of polyethylene terephthalate and 35% of cotton as a warp and a weft. A soil resistant fiber structure was obtained in the same manner as in Example 1, except that a white fabric obtained by dyeing the obtained plain weave fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 3 by gray scale for assessing staining. Based on the same principle as in Example 1, the soil resistant fiber structure had both the high soil release property and washing durability.

Example 11

A plain weave fabric was woven using 34's count two-fold yarns made from 65% of polyethylene terephthalate and 35% of cotton as a warp and a weft. A soil resistant fiber structure was obtained in the same manner as in Example 4, except that a white fabric obtained by dyeing the obtained plain weave fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 3 by gray scale for assessing staining. Based on the same principle as in Example 1, the soil resistant fiber structure had both the high soil release property and washing durability.

Example 12

A plain weave fabric was woven using 34's count two-fold yarns made from 65% of polyethylene terephthalate and 35% of cotton as a warp and a weft. A soil resistant fiber structure was obtained in the same manner as in Example 5, except that a white fabric obtained by dyeing the obtained plain weave fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 3 by gray scale for assessing staining. Based on the same principle as in Example 1, the soil resistant fiber structure had both the high soil release property and washing durability.

Example 13

A plain weave fabric was woven using 34's count two-fold yarns made from 65% by weight of polyethylene terephthalate and 35% by weight of cotton as a warp and a weft. A soil resistant fiber structure was obtained in the same manner as in Example 9, except that a white fabric obtained by dyeing the obtained plain weave fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 14

A plain weave fabric was woven using 34's count two-fold yarns made from 65% by weight of polyethylene terephthalate and 35% by weight of cotton as a warp and a weft. The obtained plain weave fabric was dyed in an ordinary dyeing process to produce a white fabric.

Then, 60 g/L of (A) PARASIN KFS-100 (a fluororesin manufactured by KEIHIN CHEMICAL CO., LTD., solid content: 10%) containing, as polymerization components, perfluorooctyl methacrylate and polyethylene glycol as a fluororesin, 100 g/L of (R) an aqueous dimethylol dihydroxy ethylene urea resin solution (solid content: 20%), and 20 g/L of (S) magnesium chloride as a catalyst were diluted to adjust a treatment liquid. The white fabric produced as described above was immersed in the treatment liquid, squeezed with a mangle to a squeezing rate of 90%, dried at a temperature of 130° C., and then heat-treated at a temperature of 170° C. to give a soil resistant fiber structure. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 15

A serge fabric was woven using 40's count two-fold yarns made from 80% by weight of polyethylene terephthalate and 20% by weight of wool as a warp and a weft. A soil resistant fiber structure was obtained in the same manner as in Example 1, except that a white fabric obtained by dyeing the obtained serge fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 16

A serge fabric was woven using 40's count two-fold yarns made from 80% by weight of polyethylene terephthalate and 20% by weight of wool as a warp and a weft. A soil resistant fiber structure was obtained in the same manner as in Example 4, except that a white fabric obtained by dyeing the obtained serge fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 17

A serge fabric was woven using 40's count two-fold yarns made from 80% by weight of polyethylene terephthalate and 20% by weight of wool as a warp and a weft. A soil resistant fiber structure was obtained in the same manner as in Example 5, except that a white fabric obtained by dyeing the obtained serge fabric in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 18

A satin knit was knitted using finished yarns made from nylon having a total fineness of 44 dtex and composed of 36 filaments. A soil resistant fiber structure was obtained in the same manner as in Example 1, except that a white fabric obtained by dyeing the obtained satin knit in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 19

A jersey knit was knitted using yarns made from 50 d nylon finished yarns and 20 d spandex, which had been subjected to false twisting and included 50% of S-twisted yarns and 50% of Z-twisted yarns. A soil resistant fiber structure was obtained in the same manner as in Example 1, except that a white fabric obtained by dyeing the obtained jersey knit in an ordinary dyeing process was used. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 by gray scale for assessing staining. Based on the same principle as in Example 1, the soil resistant fiber structure had both the high soil release property and washing durability.

Example 20

A plain weave fabric was woven using spun yarns made from polyethylene terephthalate having a total fineness of 41's count as a warp and a weft. The obtained plain weave fabric was scoured in a scouring machine at a temperature of 95° C. by a routine methop, washed with hot water, and then dried at a temperature of 130° C. Then, the plain weave fabric was dyed with a liquor flow dyeing machine to fluorescent white at a temperature of 130° C., washed by a routine method, washed with hot water, dried, and heated at a temperature of 170° C. to produce a white fabric.

Then, 60 g/L of (A) PARASIN KFS-100 (a fluororesin manufactured by KEIHIN CHEMICAL CO., LTD., solid content: 10%) containing perfluorooctyl methacrylate and polyethylene glycol as polymerization components, 3.0 g/L of (L) "BECKAMINE" (registered trademark) M-3 (a triazine ring-containing compound manufactured by DIC Corporation, solid content: 80%), and 3.0 g/L of (N) ammonium persulfate were dissolved to adjust a treatment liquid. The white fabric produced as described above was immersed in the treatment liquid, squeezed with a mangle to a squeezing rate of 90%, treated at a temperature of 100° C. in saturated steam, dried at a temperature of 130° C., and then heat-treated at a temperature of 170° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. The fluorine compound adhered to the fibers repelled the soil, and a region of polyethylene glycol forming circular dyed regions having a maximum diameter of 100 nm or more and 500 nm or less included in the fluorine compound maintained the affinity to the washing liquid during the washing without affecting the affinity of the fluorine compound to the fiber surface. Accordingly, the plain weave fabric had both the high soil release property and washing durability.

Example 21

A plain weave fabric was woven using 34's count two-fold yarns made from 65% of polyethylene terephthalate and 35% of cotton as a warp and a weft. The obtained plain weave fabric was dyed in an ordinary dyeing process to produce a white fabric.

Then, 60 g/L of (A) PARASIN KFS-100 (a fluororesin manufactured by KEIHIN CHEMICAL CO., LTD., solid content: 10%) containing perfluorooctyl methacrylate and polyethylene glycol as polymerization components, 3.0 g/L of (L) "BECKAMINE" (registered trademark) M-3 (a triazine ring-containing compound manufactured by DIC Corporation, solid content: 80%), and 3.0 g/L of (N) ammonium persulfate were dissolved to adjust a treatment liquid. The white fabric produced as described above was immersed in the treatment liquid, squeezed with a mangle to a squeezing rate of 90%, treated at a temperature of 100° C. in saturated steam, dried at a temperature of 130° C., and then heat-treated at a temperature of 170° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. The fluorine compound adhered to the fibers repelled the soil, and a region of polyethylene glycol forming circular dyed regions having a maximum diameter of 100 nm or more and 500 nm or less included in the fluorine compound maintained the affinity to the washing liquid during the washing without affecting the affinity of the fluorine compound to the fiber surface. Accordingly, the plain weave fabric had both the high soil release property and washing durability.

Example 22

A plain weave fabric was woven using spun yarns made from polyethylene terephthalate having a total fineness of 41's count as a warp and a weft. The obtained plain weave fabric was scoured in a scouring machine at a temperature of 95° C. by a routine method, washed with hot water, and then dried at a temperature of 130° C. Then, the plain weave fabric was dyed with a liquor flow dyeing machine to fluorescent white at a temperature of 130° C., washed by a routine method, washed with hot water, dried, and heated at a temperature of 170° C. to produce a white fabric.

Then, 60 g/L of (A) PARASIN KFS-100 (a fluororesin manufactured by KEIHIN CHEMICAL CO., LTD., solid content: 10%)
containing perfluorooctyl methacrylate and polyethylene glycol as polymerization components, 3.0 g/L of (L) "BECKAMINE" (registered trademark) M-3 (a triazine ring-containing compound manufactured by DIC Corporation, solid content: 80%), and 0.5 g/L of (M) Catalyst ACX (a catalyst manufactured by DIC Corporation, solid content: 35%) were dissolved to adjust a treatment liquid. The white fabric produced as described above was immersed in the treatment liquid, squeezed with a mangle to a squeezing rate of 90%, and then heat-treated at a temperature of 190° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. The fluorine compound adhered to the fibers repelled the soil, and a region of polyethylene glycol forming circular dyed regions having a maximum diameter of 100 nm or more and 500 nm or less included in the fluorine compound maintained the affinity to the washing liquid during the washing without affecting the affinity of the fluorine compound to the fiber surface. Accordingly, the plain weave fabric had both the high soil release property and washing durability.

Example 23

A plain weave fabric was woven using 34's count two-fold yarns made from 65% of polyethylene terephthalate and 35% of cotton as a warp and a weft. The obtained plain weave fabric was dyed in an ordinary dyeing process to produce a white fabric.

Then, 60 g/L of (A) PARASIN KFS-100 (a fluororesin manufactured by KEIHIN CHEMICAL CO., LTD., solid content: 10%) containing perfluorooctyl methacrylate and polyethylene glycol as polymerization components, 3.0 g/L of (L) "BECKAMINE" (registered trademark) M-3 (a triazine ring-containing compound manufactured by DIC Corporation, solid content: 80%), and 0.5 g/L of (M) Catalyst ACX (a catalyst manufactured by DIC Corporation, solid content: 35%) were dissolved to adjust a treatment liquid. The white fabric produced as described above was immersed in the treatment liquid, squeezed with a mangle to a squeezing rate of 90%, and then heat-treated at a temperature of 190° C. A region of polyethylene glycol forming a plurality of circular dyed regions having a maximum diameter of 100 nm or more and 500 nm or less included in the fluorine compound was confirmed. The soil release property of the obtained soil resistant fiber structure after 50 times of industrial wash was grade 4 to 5 by gray scale for assessing staining. The fluorine compound adhered to the fibers repelled the soil, and a region of polyethylene glycol forming circular dyed regions having a maximum diameter of 100 nm or more and 500 nm or less included in the fluorine compound maintained the affinity to the washing liquid during the washing without affecting the affinity of the fluorine compound to the fiber surface. Accordingly, the plain weave fabric had both the high soil release property and washing durability.

Comparative Example 1

A soil resistant fiber structure was obtained in the same manner as in Example 1, except that 60 g/L of (D) PARASIN KFS-101 (a fluororesin manufactured by KEIHIN CHEMICAL CO., LTD., solid content: 10%) containing perfluorooctyl methacrylate and polyethylene glycol as polymerization components was used as the fluororesin. The soil release property of the obtained fiber structure after 50 times of industrial wash was grade 2 to 3 by gray scale for assessing staining. Although the fluororesin adhered to the fibers repelled the soil, the affinity to the washing liquid during the washing was low, and satisfactory soil release property was not obtained because the maximum diameter of dyed regions formed of polyethylene glycol included in the fluororesin were less than 100 nm.

Comparative Example 2

A soil resistant fiber structure was obtained in the same manner as in Example 1, except that 60 g/L of (E) PARASIN KFS-102 (a fluororesin manufactured by KEIHIN CHEMICAL CO., LTD., solid content: 10%) containing perfluorooctyl methacrylate and polyethylene glycol as polymerization components was used as the fluororesin. The soil release property of the obtained fiber structure after 50 times of industrial wash was grade 2 to 3 by gray scale for assessing staining. Although the fluorine compound adhered to the fibers repelled the soil, the affinity to the washing liquid during the washing was low, and satisfactory soil release property was not obtained because the dyed regions formed of polyethylene glycol included in the fluororesin were less than 100 nm.

Comparative Example 3

A soil resistant fiber structure was obtained in the same manner as in Example 1, except that 60 g/L of (F) PARASIN KFS-200 (a fluororesin manufactured by KEIHIN CHEMICAL CO., LTD., solid content: 10%) containing perfluorooctyl methacrylate and polyethylene glycol as polymerization components was used as the fluororesin. The soil release property of the obtained fiber structure after 50 times of industrial wash was grade 2 to 3 by gray scale for assessing staining. Although the fluororesin adhered to the fibers repelled the soil, the affinity to the washing liquid during the washing was low, and satisfactory soil release property was not obtained because the maximum diameter of regions formed of polyethylene glycol included in the fluororesin were less than 100 nm.

Comparative Example 4

A soil resistant fiber structure was obtained in the same manner as in Example 1, except that 30 g/L of (G) "Asahi Guard" (registered trademark) AG-1100 (a fluororesin manufactured by Asahi Glass Co., Ltd., solid content: 20%) containing perfluorooctyl methacrylate and polyethylene glycol as polymerization components was used as the fluororesin. The soil release property of the obtained fiber structure after 50 times of industrial wash was grade 2 to 3 by gray scale for assessing staining. Although the fluororesin adhered to the fibers repelled the soil, the affinity to the washing liquid during the washing was low, and satisfactory soil release property was not obtained because the regions formed of polyethylene glycol included in the fluororesin were less than 100 nm.

Comparative Example 5

A soil resistant fiber structure was obtained in the same manner as in Example 1, except that 20 g/L of (H) "Unidyne" (registered trademark) TG-5243 (manufactured by DAIKIN INDUSTRIES, LTD., solid content: 30%) containing a fluorine-based vinyl monomer having a fluoroalkyl group having 6 or less carbon atoms as a polymerization component was used as the fluororesin. The soil release property of the obtained fiber structure after 50 times of industrial wash was grade 2 to 3 by gray scale for assessing staining. Although the fluororesin adhered to the fibers repelled the soil, the affinity to the washing liquid during the washing was low, and the soil release property was poor because the dyed regions formed of polyethylene glycol included in the fluororesin were less than 100 nm.

Comparative Example 6

A soil resistant fiber structure was obtained in the same manner as in Example 1, except that 20 g/L of (I) "Unidyne" (registered trademark) TG-5521 (manufactured by DAIKIN INDUSTRIES, LTD., solid content: 30%) was used as a fluororesin containing a fluorine-based vinyl monomer having a fluoroalkyl group having 6 or less carbon atoms as a polymerization component. The soil release property of the obtained fiber structure after 50 times of industrial wash was grade 2 to 3 by gray scale for assessing staining. Although the fluororesin adhered to the fibers repelled the soil, the affinity to the washing liquid during the washing was low, and satisfactory soil release property was not obtained because the dyed regions formed of polyethylene glycol included in the fluororesin were less than 100 nm.

Comparative Example 7

A soil resistant fiber structure was obtained in the same manner as in Example 1, except that 30 g/L of (J) "Asahi Guard" (registered trademark) AG-E092 (a fluororesin manufactured by Asahi Glass Co., Ltd., solid content: 20%) was used as a fluororesin containing a fluorine-based vinyl monomer having a fluoroalkyl group having 6 or less carbon atoms as a polymerization component. The soil release property of the obtained fiber structure after 50 times of industrial wash was grade 2 to 3 by gray scale for assessing staining. Although the fluororesin adhered to the fibers repelled the soil, the affinity to the washing liquid during the washing was low, and satisfactory soil release property was not obtained because the dyed regions formed of polyethylene glycol included in the fluororesin were less than 100 nm.

Comparative Example 8

A soil resistant fiber structure was obtained in the same manner as in Example 1, except that 20 g/L of (K) "Max Guard" (registered trademark) FX-2500T (a fluororesin manufactured by Kyokenkasei, solid content: 30%) was used as a fluororesin containing a fluorine-based vinyl monomer having a fluoroalkyl group having 6 or less carbon atoms as a polymerization component. The soil release property of the obtained fiber structure after 50 times of industrial wash was grade 2 by gray scale for assessing staining. Although the fluororesin adhered to the fibers repelled the soil, the affinity to the washing liquid during the washing was low, and satisfactory soil release property was not obtained because the dyed regions formed of polyethylene glycol included in the fluororesin were less than 100 nm.

Comparative Example 9

A twill fabric was woven using false twisted yarns made from polyethylene terephthalate having a total fineness of 84 dtex and composed of 72 filaments as a warp and a weft.
Then, as an antibacterial agent, 50 g of (O) 2-pyridylthiol-1-oxide zinc, 20 g of (P) a naphthalenesulfonic acid formalin condensate, and 30 g of (Q) sodium lignin sulfonate were slurried together with 300 g of water. Then, the slurry was subjected to a wet milling process with glass beads to give a colloidal composition having an average particle size of 1 μm. The test fabric was immersed in a liquid of pH 5 having a bath ratio of 1:10 and containing 1% owf of the colloidal antibacterial agent, 2% owf of a fluorescent whitish dispersive dye, and 0.5 g/L of a level dyeing agent, and dyed by a routine method under the conditions of 130° C. and 60 minutes. Then, the fabric was washed with water and dried at 170° C. for 2 minutes to give an antibacterial fabric. The soil release property of the obtained fiber structure after 50 times of industrial wash was grade 1 by gray scale for assessing staining. Since the fluororesin did not adhere to the fibers, the fibers did not repel the soil, and satisfactory soil release property was not obtained.

Comparative Example 10

A twill fabric was woven using false twisted yarns made from polyethylene terephthalate having a total fineness of 84 dtex and composed of 72 filaments as a warp and a weft. The obtained twill fabric was scoured in a scouring machine at a temperature of 95° C. by a routine method, washed with hot water, and then dried at a temperature of 130° C. Then, the twill fabric was dyed with a liquor flow dyeing machine to fluorescent white at a temperature of 130° C., washed by a routine method, washed with hot water, dried, and heated at a temperature of 170° C. to produce a white fabric.

Then, 50 g/L of (O) 2-pyridylthiol-1-oxide zinc as an antibacterial agent was diluted to adjust a treatment liquid. The white fabric produced as described above was immersed in the treatment liquid, squeezed with a mangle to a squeezing rate of 90%, dried at a temperature of 120° C., and then heat-treated at a temperature of 170° C. The soil release property of the obtained fiber structure after 50 times of industrial wash was grade 1 by gray scale for assessing staining. Since the fluororesin did not adhere to the fibers, the fibers did not repel the soil, and satisfactory soil release property was not obtained.

Comparative Example 11

A twill fabric was woven using 34's count two-fold yarns made from 80% by weight of polyethylene terephthalate and 20% by weight of cotton as a warp, and false twisted yarns made from polyethylene terephthalate having a total fineness of 84 dtex and composed of 72 filaments as a weft. A white fabric was produced by dyeing the obtained twill fabric in an ordinary dyeing process.

Then, 100 g/L of (R) an aqueous dimethylol dihydroxy ethylene urea resin solution (solid content: 20%) as a cross-linking agent, and 20 g/L of (S) magnesium chloride as a catalyst were diluted to adjust a treatment liquid. The white fabric produced as described above was immersed in the treatment liquid, squeezed with a mangle to a squeezing rate of 90%, dried at a temperature of 100° C., and then heat-treated at a temperature of 170° C. The soil release property of the obtained fiber structure after 50 times of industrial wash was grade 1 by gray scale for assessing staining. Since the fluororesin did not adhere to the fibers, the fibers did not repel the soil, and satisfactory soil release property was not obtained.

In Examples 1 to 23 and Comparative Examples 1 to 11 described above, the following fluororesins were used, and the concentration was adjusted so that the amount of the adhered fluororesin would be 0.77% based on the fiber weight in terms of solid content. In the fluororesins used in comparative examples, the amount of polyethylene glycol in the hydrophilic side chain included in the fluororesin is inappropriate.

(A) PARASIN KFS-100 (a fluororesin manufactured by KEIHIN CHEMICAL CO., LTD., solid content: 10%, containing PEG)

(B) PARARESIN NC-305 (a fluororesin manufactured by Ohara Paragium Chemical Co., Ltd., solid content: 10%, containing PEG)

(C) PARASIN KFS-150 (a fluororesin manufactured by KEIHIN CHEMICAL CO., LTD., solid content: 10%, containing PEG)

(D) PARASIN KFS-101 (a fluororesin manufactured by KEIHIN CHEMICAL CO., LTD., solid content: 10%, containing PEG)

(E) PARASIN KFS-102 (a fluororesin manufactured by KEIHIN CHEMICAL CO., LTD., solid content: 10%, containing PEG)

(F) PARASIN KFS-200 (a fluororesin manufactured by KEIHIN CHEMICAL CO., LTD., solid content: 10%, containing PEG)

(G) "Asahi Guard" (registered trademark) AG-1100 (a fluororesin manufactured by Asahi Glass Co., Ltd., solid content: 20%, containing PEG)

(H) "Unidyne" (registered trademark) TG-5243 (manufactured by DAIKIN INDUSTRIES, LTD., solid content: 30%, PEG-free)

(I) "Unidyne" (registered trademark) TG-5521 (manufactured by DAIKIN INDUSTRIES, LTD., solid content: 30%, PEG-free)

(J) "Asahi Guard" (registered trademark) AG-E092 (a fluororesin manufactured by Asahi Glass Co., Ltd., solid content: 20%, PEG-free)

(K) "Max Guard" (registered trademark) FX-2500T (a fluororesin manufactured by Kyokenkasei, solid content: 30%, PEG-free)

In addition, (L) and (M) were respectively used as a cross-linking agent for the fluorine compound and a catalyst.

(L) "BECKAMINE" (registered trademark) M-3 (a triazine ring-containing compound manufactured by DIC Corporation, solid content: 80%)

(M) Catalyst ACX (a catalyst manufactured by DIC Corporation, solid content: 35%)

(N) Ammonium persulfate

In addition, the following agents (N) to (P) were used for imparting antibacterial properties.

(O) 2-Pyridylthiol-1-oxide zinc (P) Naphthalenesulfonic acid formalin condensate (Q) Sodium lignin sulfonate In addition, the following agents (R) to (S) were used for imparting washing durability to a fabric made from synthetic fibers blended with a natural material.

(R) Dimethylol dihydroxy ethylene urea (S) Magnesium chloride

The treatment liquid compositions (A) to (S) and fiber materials of Examples 1 to 23 and Comparative Examples 1 to 11 are shown in Table 2.

TABLE 2

| | SoilResistant Property Treatment Treatment Liquid Composition (g/L) | | | | | | | | | | | | | | Antibacterial Property Treatment | | | Cross-linking Modification | | Fiber |
|---|---|---|---|---|---|---|---|---|---|---|---|---|---|---|---|---|---|---|---|---|
| | A | B | C | D | E | F | G | H | I | J | K | L | M | N | O | P | Q | R | S | material |
| Example 1 | 60 | | | | | | | | | | | 3 | 0.5 | | | | | | | PET100 |
| Example 2 | | 60 | | | | | | | | | | 3 | 0.5 | | | | | | | |
| Example 3 | | | 60 | | | | | | | | | 3 | 0.5 | | | | | | | |
| Example 4 | 60 | | | | | | | | | | | 3 | 0.5 | | 50 | 20 | 30 | | | |
| Example 5 | 60 | | | | | | | | | | | 3 | 0.5 | | 50 | | | | | |
| Example 6 | 60 | | | | | | | | | | | 3 | 0.5 | | | | | | | PET80/C |
| Example 7 | 60 | | | | | | | | | | | 3 | 0.5 | | 50 | 20 | 30 | | | |
| Example 8 | 60 | | | | | | | | | | | 3 | 0.5 | | 50 | | | | | |
| Example 9 | 60 | | | | | | | | | | | 3 | 0.5 | | | | | 100 | 20 | |
| Example 10 | 60 | | | | | | | | | | | 3 | 0.5 | | | | | | | PET65/C |
| Example 11 | 60 | | | | | | | | | | | 3 | 0.5 | | 50 | 20 | 30 | | | |
| Example 12 | 60 | | | | | | | | | | | 3 | 0.5 | | 50 | | | | | |
| Example 13 | 60 | | | | | | | | | | | 3 | 0.5 | | | | | 100 | 20 | |
| Example 14 | 60 | | | | | | | | | | | 3 | 0.5 | | | | | 100 | 20 | |
| Example 15 | 60 | | | | | | | | | | | 3 | 0.5 | | | | | | | PET80/W |
| Example 16 | 60 | | | | | | | | | | | 3 | 0.5 | | 50 | 20 | 30 | | | |
| Example 17 | 60 | | | | | | | | | | | 3 | 0.5 | | 50 | | | | | |
| Example 18 | 60 | | | | | | | | | | | 3 | 0.5 | | | | | | | Ny100 |
| Example 19 | 60 | | | | | | | | | | | 3 | 0.5 | | | | | | | Ny70/PU |
| Example 20 | 60 | | | | | | | | | | | 3 | | 3 | | | | | | PET100 |
| Example 21 | 60 | | | | | | | | | | | 3 | | 3 | | | | | | PET65/C |
| Example 22 | 60 | | | | | | | | | | | 3 | 0.5 | | | | | | | PET100 |
| Example 23 | 60 | | | | | | | | | | | 3 | 0.5 | | | | | | | PET65/C |
| Comparative Example 1 | | | 60 | | | | | | | | | 3 | 0.5 | | | | | | | PET100 |
| Comparative Example 2 | | | | 60 | | | | | | | | 3 | 0.5 | | | | | | | |
| Comparative Example 3 | | | | | 60 | | | | | | | 3 | 0.5 | | | | | | | |
| Comparative Example 4 | | | | | | 30 | | | | | | 3 | 0.5 | | | | | | | |
| Comparative Example 5 | | | | | | | | 20 | | | | 3 | 0.5 | | | | | | | |
| Comparative Example 6 | | | | | | | | | 20 | | | 3 | 0.5 | | | | | | | |
| Comparative Example 7 | | | | | | | | | | 30 | | 3 | 0.5 | | | | | | | |
| Comparative Example 8 | | | | | | | | | | | 20 | 3 | 0.5 | | | | | | | |
| Comparative Example 9 | | | | | | | | | | | | | | | 50 | 20 | 30 | | | |
| Comparative Example 10 | | | | | | | | | | | | | | | 50 | | | | | |
| Comparative Example 11 | | | | | | | | | | | | | | | | | | 100 | 20 | |

The results of performance and the like of the fiber structures obtained in Examples 1 to 23 and Comparative Examples 1 to 11 are shown in Tables 3, 4, and 5. The grade numbers in parentheses of water repellency in Table 4 indicate that the back of the test fabric is also wet.

TABLE 3

| | Maximum diameter of the region dyed with osmium oxide as oberserved with TEM (nm) | Mass concentration of oxigen atoms (mass %)/ Mass concentration of fluorine atoms (mass %) |
|---|---|---|
| Example 1 | 130 | 3.52 |
| Example 2 | 100 | 3.49 |
| Example 3 | 500 | 3.78 |
| Example 4 | 130 | 3.52 |
| Example 5 | 130 | 3.52 |
| Example 6 | 130 | 3.52 |
| Example 7 | 130 | 3.52 |
| Example 8 | 130 | 3.52 |
| Example 9 | 130 | 3.52 |
| Example 10 | 130 | 3.52 |
| Example 11 | 130 | 3.52 |
| Example 12 | 130 | 3.52 |
| Example 13 | 130 | 3.52 |
| Example 14 | 130 | 3.52 |
| Example 15 | 130 | 3.52 |
| Example 16 | 130 | 3.52 |
| Example 17 | 130 | 3.52 |
| Example 18 | 130 | 3.52 |
| Example 19 | 130 | 3.52 |
| Example 20 | 130 | 3.52 |
| Example 21 | 130 | 3.52 |
| Example 22 | 130 | 3.52 |
| Example 23 | 130 | 3.52 |
| Comparative Example 1 | 90 | 3.45 |

TABLE 3-continued

| | Maximum diameter of the region dyed with osmium oxide as observed with TEM (nm) | Mass concentration of oxygen atoms (mass %)/ Mass concentration of fluorine atoms (mass %) |
|---|---|---|
| Comparative Example 2 | 90 | 3.43 |
| Comparative Example 3 | 40 | 3.47 |
| Comparative Example 4 | 90 | 2.03 |
| Comparative Example 5 | 50 | 2.12 |
| Comparative Example 6 | 50 | 2.58 |
| Comparative Example 7 | 40 | 2.34 |
| Comparative Example 8 | 40 | 2.03 |
| Comparative Example 9 | — | — (no fluorine atom) |
| Comparative Example 10 | — | — (no fluorine atom) |
| Comparative Example 11 | — | — (no fluorine atom) |

TABLE 4

| | Water repellency (grade) | Oil repellency (grade) | Soil Release Property (grade) | Soil Release Test (grade) | Antibacterial Property Before wash | Antibacterial Property After 50 times of industial wash | Prevention of Bleeding Property |
|---|---|---|---|---|---|---|---|
| Example 1 | 2 | 6 | 4-5 | 4-5 | failure | failure | good |
| Example 2 | 2 | 6 | 4 | 3-4 | failure | failure | good |
| Example 3 | 1 | 6 | 4 | 3 | failure | failure | failure |
| Example 4 | 2 | 6 | 4-5 | 4-5 | good | good | good |
| Example 5 | 2 | 6 | 4-5 | 4-5 | good | good | good |
| Example 6 | 2 | 6 | 4 | 4 | failure | failure | good |
| Example 7 | 2 | 6 | 4 | 4 | good | good | good |
| Example 8 | 2 | 6 | 4 | 4 | good | good | good |
| Example 9 | 2 | 6 | 4-5 | 4-5 | failure | failure | good |
| Example 10 | 2 | 6 | 3-4 | 3 | failure | failure | good |
| Example 11 | 2 | 6 | 3-4 | 3 | good | good | good |
| Example 12 | 2 | 6 | 3-4 | 3 | good | good | good |
| Example 13 | 2 | 6 | 4 | 4 | failure | failure | good |
| Example 14 | 2 | 6 | 4 | 4 | failure | failure | good |
| Example 15 | 2 | 6 | 4 | 4 | failure | failure | good |
| Example 16 | 2 | 6 | 4 | 4 | good | good | good |
| Example 17 | 2 | 6 | 4 | 4 | good | good | good |
| Example 18 | 2 | 6 | 4-5 | 4-5 | failure | failure | good |
| Example 19 | 2 | 6 | 4-5 | 4-5 | failure | failure | good |
| Example 20 | 2 | 7 | 4-5 | 4-5 | failure | failure | good |
| Example 21 | 2 | 7 | 4-5 | 4-5 | failure | failure | good |
| Example 22 | 2 | 7 | 4-5 | 4-5 | failure | failure | good |
| Example 23 | 2 | 7 | 4-5 | 4-5 | failure | failure | good |
| Comparable Example 1 | 3 | 6 | 3 | 2-3 | failure | failure | good |
| Comparative Example 2 | 3 | 6 | 3 | 2-3 | failure | failure | good |
| Comparative Example 3 | 3-4 | 6 | 3 | 2-3 | failure | failure | good |
| Comparative Example 4 | 2-3 | 6 | 3 | 2-3 | failure | failure | failure |
| Comparative Example 5 | 4-5 | 7 | 3 | 2-3 | failure | failure | failure |
| Comparative Example 6 | 4-5 | 6 | 3 | 2-3 | failure | failure | failure |
| Comparative Example 7 | 5 | 6-7 | 3 | 2-3 | failure | failure | failure |
| Comparative Example 8 | 5 | 7 | 2-3 | 2 | failure | failure | failure |
| Comparative Example 9 | (1) | — | 1 | 1 | good | good | failure |
| Comparative Example 10 | (1) | — | 1 | 1 | good | good | failure |
| Comparative Example 11 | (1) | — | 1 | 1 | failure | failure | failure |

TABLE 5

| | Minimum MA value for achieving Soil Release Property of 4th Grade | Amount of greenhouse gas reduction by shortening of washing time (kgCO$_2$-eq) | Amount of greenhouse gas reduction by reduction of detergent amount (KgCO$_2$-eq) |
|---|---|---|---|
| Example 1 | 19 | 0.47 | 0.44 |
| Example 2 | 51 | 0 | 0 |
| Example 3 | 51 | 0 | 0 |
| Example 4 | 19 | 0.47 | 0.44 |
| Example 5 | 19 | 0.47 | 0.44 |
| Example 6 | 19 | 0.47 | 0.44 |
| Example 7 | 19 | 0.47 | 0.44 |
| Example 8 | 19 | 0.47 | 0.44 |
| Example 9 | 19 | 0.47 | 0.44 |
| Example 10 | 51 | 0 | 0 |
| Example 11 | 51 | 0 | 0 |
| Example 12 | 51 | 0 | 0 |
| Example 13 | 51 | 0 | 0 |
| Example 14 | 51 | 0 | 0 |
| Example 15 | 51 | 0 | 0 |
| Example 16 | 51 | 0 | 0 |
| Example 17 | 51 | 0 | 0 |
| Example 18 | 51 | 0 | 0 |
| Example 19 | 51 | 0 | 0 |
| Example 20 | 19 | 0.47 | 0.44 |
| Example 21 | 19 | 0.47 | 0.44 |
| Example 22 | 19 | 0.47 | 0.44 |
| Example 23 | 19 | 0.47 | 0.44 |
| Comparative Example 1 | 51 | 0 | 0 |
| Comparative Example 2 | 51 | 0 | 0 |
| Comparative Example 3 | 51 | 0 | 0 |
| Comparative Example 4 | 51 | 0 | 0 |
| Comparative Example 5 | 51 | 0 | 0 |
| Comparative Example 6 | 51 | 0 | 0 |
| Comparative Example 7 | 51 | 0 | 0 |
| Comparative Example 8 | 51 | 0 | 0 |
| Comparative Example 9 | 51 | 0 | 0 |
| Comparative Example 10 | 51 | 0 | 0 |
| Comparative Example 11 | 51 | 0 | 0 |

As is apparent from Table 3, in Examples 1 to 23 which are the fiber structures of the present invention, the maximum diameter of the dyed regions of the hydrophilic component is 100 to 500 nm, and the fiber structure is excellent in soil release property. In contrast, in Comparative Examples 1 to 11 which are different from the soil resistant fiber structure of the present invention, the maximum diameter of the dyed regions of the hydrophilic component is less than 100 nm, so that the fiber structures are inferior in soil release property to those in the examples.

The soil resistant fiber structure of the present invention is suitably used in general clothing items, working uniforms, bedding products, medical garments, interior goods, industrial materials and the like, since the fiber structure has both high anti-adhesion property against aqueous soils and oily soils and soil release property by washing. Above all, the soil resistant fiber structure is suitably used in working uniforms which are likely to catch oily soils hardly releasable by washing and are required to have soil resistance.

The invention claimed is:

1. A soil resistant fiber structure, comprising a fiber and a soil resistant resin fixed to at least a part of a surface of the fiber,
   wherein the resin has, in at least a part inside the resin, one or more regions dyed with osmium oxide as observed with a transmission electron microscope,
   at least one of the regions is circular,
   the regions have a maximum diameter of 100 nm or more and 500 nm or less, and
   the soil resistant fiber structure has a mass concentration ratio of oxygen atoms to fluorine atoms (O/F) of 3 or more as obtained by measuring the surface of the fiber with an energy dispersive X-ray analyzer.

2. The soil resistant fiber structure according to claim 1, wherein the resin has a plurality of the regions inside the resin, and the dyed regions are individually separated and scattered.

3. The soil resistant fiber structure according to claim 2, wherein the regions have a hydrophilic component and a hydrophobic component.

4. The soil resistant fiber structure according to claim 3, wherein the hydrophilic component is polyethylene glycol.

5. The soil resistant fiber structure according to claim 1, wherein the resin has a perfluorooctanoic acid content less than a detection limit.

6. The soil resistant fiber structure according to claim 5, wherein the resin contains a compound represented by the following general formula (I) as a polymerization component:

$$CH_2=C(CH_3)C(=O)OCH_2CH_2(CF_2)_5CF_3 \qquad (I).$$

7. The soil resistant fiber structure according to claim 1, having a soil release property in a soil release test of grade 3 or higher after 50 times of industrial wash.

* * * * *

UNITED STATES PATENT AND TRADEMARK OFFICE
CERTIFICATE OF CORRECTION

PATENT NO. : 10,513,820 B2
APPLICATION NO. : 15/736049
DATED : December 24, 2019
INVENTOR(S) : Otsuka et al.

Page 1 of 1

It is certified that error appears in the above-identified patent and that said Letters Patent is hereby corrected as shown below:

On the Title Page

Item [72], Inventors:

"Azuki Otsuka, Osaka (JP)" should read --Azuki Otsuka, Osaka-shi, Osaka (JP)--.

"Shinya Komori, Otsu (JP)" should read --Shinya Komori, Otsu-shi, Shiga (JP)--.

"Rumi Karasawa, Otsu (JP)" should read --Rumi Karasawa, Otsu-shi, Shiga (JP)--.

"Keiji Takeda, Otsu (JP)" should read --Keiji Takeda, Otsu-shi, Shiga (JP)--.

Signed and Sealed this
Eighteenth Day of August, 2020

Andrei Iancu
*Director of the United States Patent and Trademark Office*